United States Patent
Nichols et al.

(10) Patent No.: US 11,158,400 B2
(45) Date of Patent: Oct. 26, 2021

(54) AUTONOMOUS REASONING AND EXPERIMENTATION AGENT FOR MOLECULAR DISCOVERY

(71) Applicant: General Electric Company, Schenectady, NY (US)

(72) Inventors: Jason Nichols, Niskayuna, NY (US); Johan Michael Reimann, Clifton Park, NY (US); Nurali Virani, Niskayuna, NY (US); Naresh Sundaram Iyer, Ballston Spa, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 111 days.

(21) Appl. No.: 16/739,239

(22) Filed: Jan. 10, 2020

(65) Prior Publication Data
US 2020/0227142 A1 Jul. 16, 2020

Related U.S. Application Data

(60) Provisional application No. 62/791,176, filed on Jan. 11, 2019.

(51) Int. Cl.
*G16C 20/20* (2019.01)
*G16C 20/70* (2019.01)
(Continued)

(52) U.S. Cl.
CPC ............. *G16C 20/20* (2019.02); *G06N 7/005* (2013.01); *G06N 20/00* (2019.01); *G16C 20/70* (2019.02)

(58) Field of Classification Search
None
See application file for complete search history.

(56) References Cited

U.S. PATENT DOCUMENTS

| | | |
|---|---|---|
| 5,526,281 A | 6/1996 | Chapman et al. |
| 6,762,025 B2 | 7/2004 | Cubicciotti |

(Continued)

OTHER PUBLICATIONS

Herron et al. ("Text Mining Adoption for Pharmacogenomics-based Drug Discovery in a Large Pharmaceturical Company: a Case study", University of North Carolina, Chapel Hill, 2006). (Year: 2006).*

(Continued)

*Primary Examiner* — Roy Y Yi
(74) *Attorney, Agent, or Firm* — Buckley, Maschoff & Talwalkar LLC

(57) ABSTRACT

According to some embodiments, a system, method and non-transitory computer-readable medium are provided comprising a Hypothesis Generation Engine (HGE) to receive one or more property target values for a material; a memory for storing program instructions; an HGE processor, coupled to the memory, and in communication with the HGE, and operative to execute program instructions to: receive the one or more property target values for the material; analyze the one or more property target values as compared to one or more known values in a knowledge base; generate, based on the analysis, an initial set of hypothetical structures, wherein each hypothetical structure includes at least one property target value; execute a likelihood model for each candidate material to generate a likelihood probability for each hypothetical structure, wherein the likelihood probability is a measure of the likelihood that the hypothetical structure will have the target property value; convert each hypothetical structure into a natural language representation; execute an abduction kernel on the natural language representation with the at least one likelihood probability, to output at least one proposed structure that satisfies a likelihood threshold for having the property target value; and receive the output of the executed abduction (Continued)

kernel at a testing module to determine whether the output satisfies the property target values. Numerous other aspects are provided.

20 Claims, 12 Drawing Sheets

(51) Int. Cl.
    *G06N 7/00*         (2006.01)
    *G06N 20/00*     (2019.01)

(56) References Cited

U.S. PATENT DOCUMENTS

| | | |
|---|---|---|
| 7,747,391 B2 | 6/2010 | Gustafsson et al. |
| 8,494,987 B2 * | 7/2013 | Katukuri ............... G16H 50/70 706/13 |
| 2005/0177280 A1 | 8/2005 | Almstetter et al. |
| 2014/0324359 A1 | 10/2014 | Smith et al. |

OTHER PUBLICATIONS

Baldi, Pierre "Exploring Chemical Space with Computers: Challenges and Opportunities", Proceedings of International Joint Conference on Neural Networks, 2005 IEEE, Montreal, Jul. 31-Aug. 4, 2005, 1pg.

Montavon, Grégoire et al., "Machine Learning of Molecular Electronic Properties in Chemical Compound Space", New Journal of Physics, vol. 15, Issue 9, May 2013, DOI: 10.1088/1367-2630/15/9/095003, (pp. 301-309, 16 total pages).

Hansen, Katja et al., "Machine Learning Predictions of Molecular Properties: Accurate Many-Body Potentials and Nonlocality in Chemical Space", The Journal of Physical Chemistry Letters, vol. 06, Issue 12, Jun. 4, 2015, DOI: 10.1021/acs.jclett.5b00831, (pp. 2326-2331, 6 total pages).

Hop, Patrick et al., "Geometric Deep Learning Autonomously Learns Chemical Features That Outperform Those Engineered by Domain Experts", Molecular Pharmaceutics, vol. 15, Issue 10, Jun. 4, 2018, DOI: 10.1021/acs.molpharmaceut.7b01144, (pp. 4371-4377, 7 total pages).

* cited by examiner

AUTONOMOUS REASONING AND EXPERIMENTATION AGENT FOR MOLECULAR DISCOVERY

CROSS REFERENCE TO RELATED APPLICATION

The present application claims priority from the following U.S. Provisional Patent Application, which is hereby incorporated by reference herein in its entirety for all purposes: U.S. Provisional Patent Application Ser. No. 62/791,176, filed Jan. 11, 2019 and entitled "AN AUTONOMOUS REASONING AND EXPERIMENTATION AGENT FOR MOLECULAR DISCOVERY".

BACKGROUND

A chemist may apply traditional combinatorial/high-throughput approaches to molecular discovery, which may require an exhaustive sampling of chemical space for success. There may be two main obstacles to discovering electrolytes, and small molecules in general: 1. high-dimensional search in structure-property mappings (i.e., chemical space) and 2. a testing bottleneck.

It would be desirable to provide systems and methods to improve the molecular discovery process.

SUMMARY

According to some embodiments, a system includes a Hypothesis Generation Engine (HGE) to receive one or more property target values for a material; a memory for storing program instructions; an HGE processor, coupled to the memory, and in communication with the HGE, and operative to execute program instructions to: receive the one or more property target values for the material; analyze the one or more property target values as compared to one or more known values in a knowledge base; generate, based on the analysis, an initial set of hypothetical structures, wherein each hypothetical structure includes at least one property target value; execute a likelihood model for each candidate material to generate a likelihood probability for each hypothetical structure, wherein the likelihood probability is a measure of the likelihood that the hypothetical structure will have the target property value; convert each hypothetical structure into a natural language representation; execute an abduction kernel on the natural language representation with the at least one likelihood probability, to output at least one proposed structure that satisfies a likelihood threshold for having the property target value; and receive the output of the executed abduction kernel at a testing module to determine whether the output satisfies the property target values.

According to some embodiments a computer-implemented method includes receiving one or more property target values for a material; analyzing the one or more property target values as compared to one or more known values in a knowledge base; generating, based on the analysis, an initial set of hypothetical structures, wherein each hypothetical structure includes at least one property target value; executing a likelihood model for each candidate material to generate a likelihood probability for each hypothetical structure, wherein the likelihood probability is a measure of the likelihood that the hypothetical structure will have the target property value; convert each hypothetical structure into a natural language representation; executing an abduction kernel on the natural language representation with the at least one likelihood probability, to output at least proposed structure that satisfies a likelihood threshold for having the property target value; and receiving the output of the executed abduction kernel at a testing module to determine whether the output satisfies the property target values.

According to some embodiments a non-transient, computer-readable medium stores instructions to be executed by a processor to perform a method including: receiving one or more property target values for a material; analyzing the one or more property target values as compared to one or more known values in a knowledge base; generating, based on the analysis, an initial set of hypothetical structures, wherein each hypothetical structure includes at least one property target value; executing a likelihood model for each candidate material to generate a likelihood probability for each hypothetical structure, wherein the likelihood probability is a measure of the likelihood that the hypothetical structure will have the target property value; convert each hypothetical structure into a natural language representation; executing an abduction kernel on the natural language representation with the at least one likelihood probability, to output at least proposed structure that satisfies a likelihood threshold for having the property target value; and receiving the output of the executed abduction kernel at a testing module to determine whether the output satisfies the property target values.

Some technical effects of some embodiments disclosed herein are improved computerized systems and computerized methods to automatically discover electrolytes and small molecules. One or more embodiments provide a hypothesis generation engine (HGE) that will yield a suitable amount (e.g., one gram) of novel and unknown small molecules that meet the property requirements for a given application by iteratively reasoning over chemical structures to generate and test novel molecular hypothesis. The HGE may yield molecules with desired physical properties with up to, as a non-exhaustive example, $10^3$ fewer calculations and synthetic targets than possible with conventional methods. One or more embodiments provide for overcoming the high dimensional search obstacle through an abductive reasoning approach. Structural hypothesis testing may be debottlenecked by deploying, in one or more embodiments, three automated testing capabilities in parallel: a literature search and extraction method based on semi-supervised natural language processing techniques, a computational search method that includes the development and then routine calculation of actionable descriptors, and a physical molecular synthesis and characterization platform to obtain structure-property observations where necessary. As a result, the HGE may, in a directed fashion, rapidly hone in on the regions of chemical space that provide the highest likelihood of success (e.g., molecules that meet the property requirements for a given application) in one or more embodiments.

One or more embodiments provide for combining a reasoning engine with a likelihood model to result in a given chemical structure that has a desired property. Embodiments may or may not necessarily predicting the property itself. It is noted that the goal of one or more embodiments is to select a testable hypothesis, and not necessarily find the molecules. One or more embodiments may try to find a collection of structures that are testable having the likelihood of having the asserted properties.

One or more embodiments provide for using reinforcement learning for generating structures along physical property vectors. One or more embodiments may create a vector in which the property is most likely to range and then use re-enforcement learning, or other suitable processes, to follow that vector and generate a structure that is likely to increase or decrease the property along that vector. The reinforcement learning may modify a given structure to get it closer to having the target properties.

With this and other advantages and features that will become hereinafter apparent, a more complete understanding of the nature of the invention can be obtained by referring to the following detailed description and to the drawings appended hereto.

Other embodiments are associated with systems and/or computer-readable medium storing instructions to perform any of the methods described herein.

DETAILED DESCRIPTION

Figure 1:
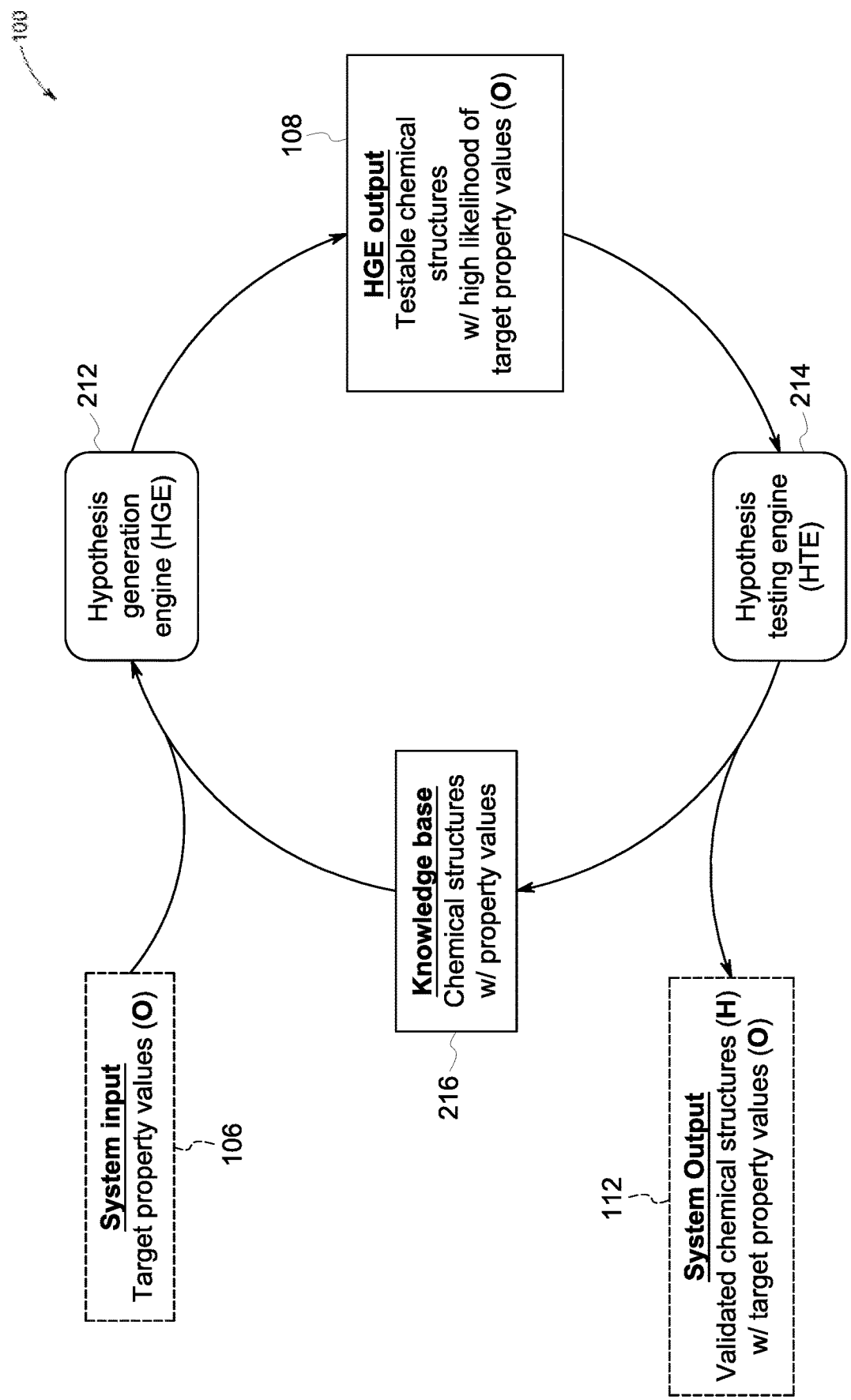
FIG. 1 is a block a diagram of a process according to some embodiments.

In the following detailed description, numerous specific details are set forth in order to provide a thorough understanding of embodiments. However, it will be understood by those of ordinary skill in the art that the embodiments may be practiced without these specific details. In other instances, well-known methods, procedures, components and circuits have not been described in detail so as not to obscure the embodiments.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Research in automated molecular discovery has focused on ever increasing capabilities to compute and synthesize compounds at large scales with millions of compounds calculated and thousands of compounds synthesized. However, this is computationally expensive and time consuming as it simply generates many compounds in a large response surface, without searching for a particular compound. Then a user has to sift through the generated compounds to find the compound(s) that best meets the needs of the user. As used herein, the terms "user" and "chemist" may be used interchangeably. Another conventional approach is for a chemist to determine, prior to the computation of compounds, a particular response space that is constrained in order to make the space tractable such that enough compounds can be made to understand how the physical property maps to structure (e.g., property-structure mapping, quantitative-structure-property-mapping); and then for the chemist to manually synthesize compounds by experimentation and optimize the resulting result surface, using a qualitative structural mapping. It is noted that a chemist has never simultaneously considered thousands of structures for compounds ("structures") in solving a molecular discovery problem. Additionally, the chemist approach is very resource (time, finances, etc.) intensive and does not use anything other than brute force statistical mapping. It is further noted that generally suggesting novel structures may not be too difficult given some atoms, a maximum character length a SMILES string generator and no constraints on plausibility, as in conventional processes. A conventional generator, however, requires constraints such as stability or plausibility to prevent the generation of useless noise. However, even with some constraints, the number of proposed structures that require computation can still approach $10'$ entities.

To resolve these problems, one or more embodiments provide for the emulation of a chemist's approach to molecular discovery but in an automated, dynamic, computational manner, so that the process can be scaled to consider more possible compound structures than is typically possible for the chemist. One or more embodiments provide for a HGE that iteratively reasons over chemical structures guided by chemo-physical properties that translate to performance. Conventionally, structural reasoning is how a chemist creates maximum structural diversity relevant to a desired outcome and reduces the high-dimensional problem of chemical space to a manageable size along a performance target vector. Using probabilistic abductive reasoning coupled to generalized likelihood models for chemical properties, one or more embodiments combine the generative aspects of abductive reasoning with the high-dimensional learning aspects of deep learning models to emulate a structure-property reasoning process of a chemist in an automated computational manner. One or more embodiments may use an action space selection process inspired by reinforcement learning systems that will constrain structure modifications to those that move a structure in a desired direction (e.g., towards a structure that has the desired physical property) along a coarse estimate of a property gradient. This may be conceptually similar to a user manually reasoning through structure modifications using linear free energy relationships, and unlike conventional computational methods, which do not progress in a directed way (e.g., the conventional computational methods simply scan as much chemical space as possible using super computers to create a massive calculation space including random structures). One or more embodiments provide for a directed action space that just includes those structures having a high likelihood of success at meeting the physical property target values of the chemist/user.

It is noted that one or more embodiments may provide for the acceleration of materials discovery and automation of self-motivated learning agents acting over high throughput chemical modeling, synthesis and characterization systems.

An HGE (e.g., abductive reasoning engine+curiosity function) may be an efficiently, self-motivated learning agent for chemical structure information. The HGE may optimally direct computational exploration via high throughput modeling. The HGE may optimally direct automated synthesis and characterization systems to create new materials. Modeling, synthesis and characterization may be automated for solid state crystalline materials, or other suitable materials.

In one or more embodiments, the HGE may be an autonomous assistant for the user that will reason over chemical structure to yield desired physical properties without explicit programming of a reasoning engine. For example, if the HGE spoke, it may say "Given what you have asserted and what I know about the application you have asserted, I can deduce a certain set of molecules that are already known from a knowledge base." If one of the molecules satisfies all of the properties, that may be considered a "search" (e.g., the HGE successfully searched the knowledge base and found something that exists." However, if the known set of molecules from the knowledge base does not cover all of the properties (e.g., maybe 3 or 4 molecules are needed to cover all the properties) then this is a partial set coverage of the property set. Then this subset of molecules form the inputs for the reinforcement learning aspect of the HGE to vary the structure and understand how close you can get to the target property values with the least amount of molecules.

In one or more embodiments, the HGE may receive one or more target property values for a target structure, and compare these target properties to one or more knowledge sources storing structures and properties associated therewith. The HGE may then receive at least one structure from the knowledge source that has one of the target property values. For example, if the structure needs a boiling point of 110 degrees Celsius, a molar solubility greater than 10 $mol/dm^3$ and a UV absorbance 400 nanometers, the HGE may analyze the structures and associated properties in the knowledge source and retrieve, for each target property value all of the structures with property values near the given target property value. Continuing with the example, the HGE retrieves all structures with a boiling point near 110 degrees Celsius, retrieves all structures with a molar solubility greater than 10 $mol/dm^3$ and retrieves all structures with a UV absorbance near 400 nanometers. Then the HGE may determine, for each of these structures, how likely it is that the given structure also has any of the other target property values associated therewith. In one or more embodiments, the HGE may then optimize the structures by taking the fewest structures with the highest likelihood of representing all of the target property values. Continuing with the example, the initial results had ten structures with boiling points near 110 degrees Celsius, eight structures with a molar solubility greater than 10 $mol/dm^3$ and seven structures with UV absorbance near 400 nanometers. Of these 25 results, three structures have the highest likelihood probability of having the target boiling point and molar solubility and two structures have the highest likelihood probability of having the target boiling point and UV absorbance. As such, the optimized structure set includes five structures. The HGE may then generates novel structures (e.g., structures other than the five structures provided here), to further reduce the optimized structure set, as described further below. It is noted that, in one or more embodiments, regarding the generation of novel structures, abductive reasoning techniques can be applied to chemical structures expressed as a natural language. The final set of optimized structures may then be tested by a testing module to determine whether they satisfy the target property values. When the set of optimized structures satisfies the target property values, the set of optimized structures is output from the testing module and may be returned to the user, otherwise the process may return to the HGE for the generation of more structures to test. It is further noted that the testing and generation of structures may be an iterative process whereby the final set of optimized structures is tested to provide feedback to the system so that a new set of structures may be generated for evaluation, to ultimately result in structures with the highest likelihood of having the desired properties. The iterative aspect may a continuous learning system whereby novel structures may be extrapolations outside of the initial set of data.

The system may include automated tools to resolve the target property values ("hypothetical assertions") in three forms: an agent to test assertions against literature reported properties, an automated computational platform to test assertions against computed properties, and an automated synthesis and characterization platform to test assertions against measured properties. The system may iteratively cycle through the reasoning workflow to generate hypothetical structures, test the property outcomes, and update the underlying models for generating new structures. In this way, the system will be an actively learning system that yields relevant information at scale.

It is noted that in the classical sense, abductive reasoning is the process a medical doctor uses to arrive at a diagnosis given a collection of symptoms. The best diagnosis is the hypothesis that most likely explains all of the symptoms in the set. One or more embodiments provide for complementing high-throughput screening methods with abductive reasoning methods to enable extrapolation in chemical space. One or more embodiments provide for the formulation of the molecular structure as the "diagnosis," the properties as the "symptoms" and then a Simplified Molecular Input Line Entry System (SMILES) may be used as the natural language in an abductive reasoning solver, including but not limited to LISP. The abduction may allow the system to extrapolate to likely molecular structures that explain most of the symptoms more quickly than optimally applying computational screening techniques.

Figure 2A:
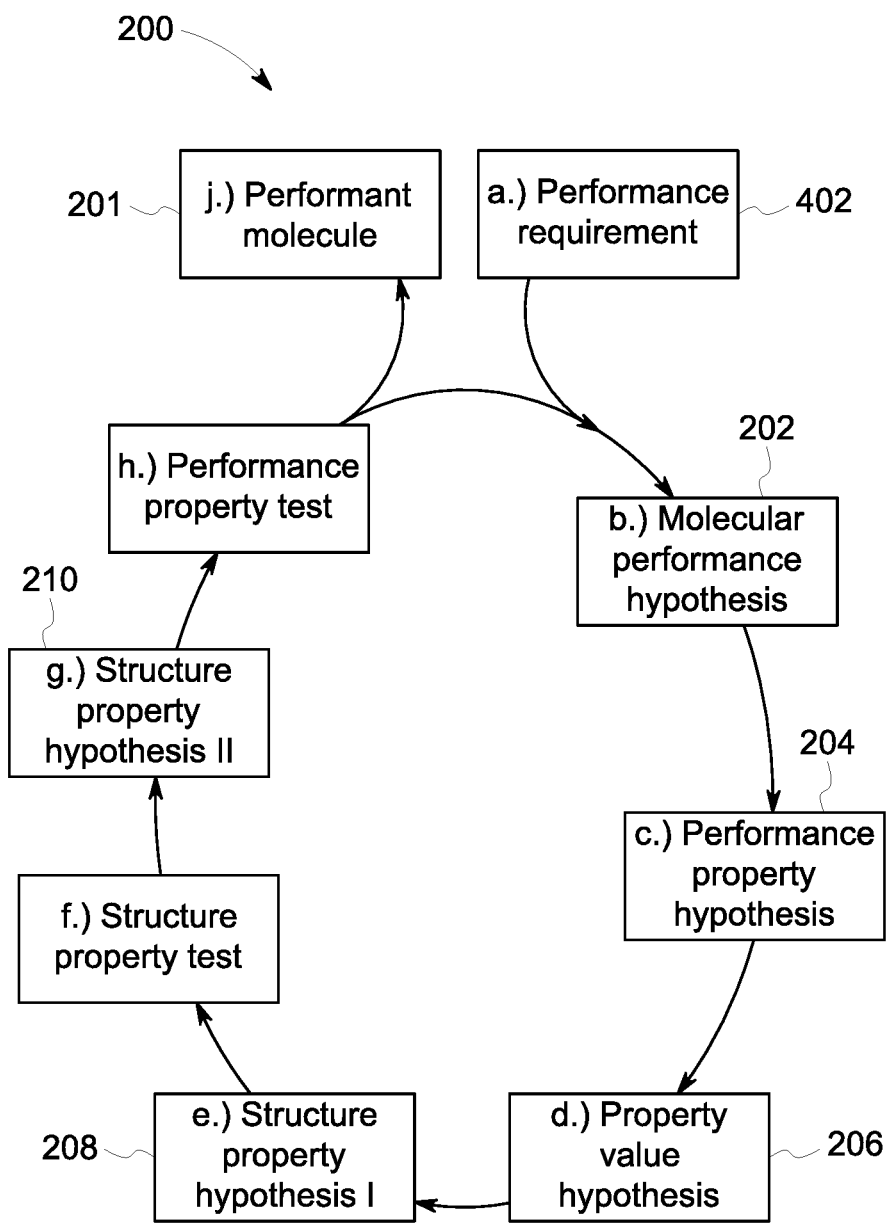
FIGS. 2A-C are block diagrams of a process according to some embodiments.
Figure 2B:
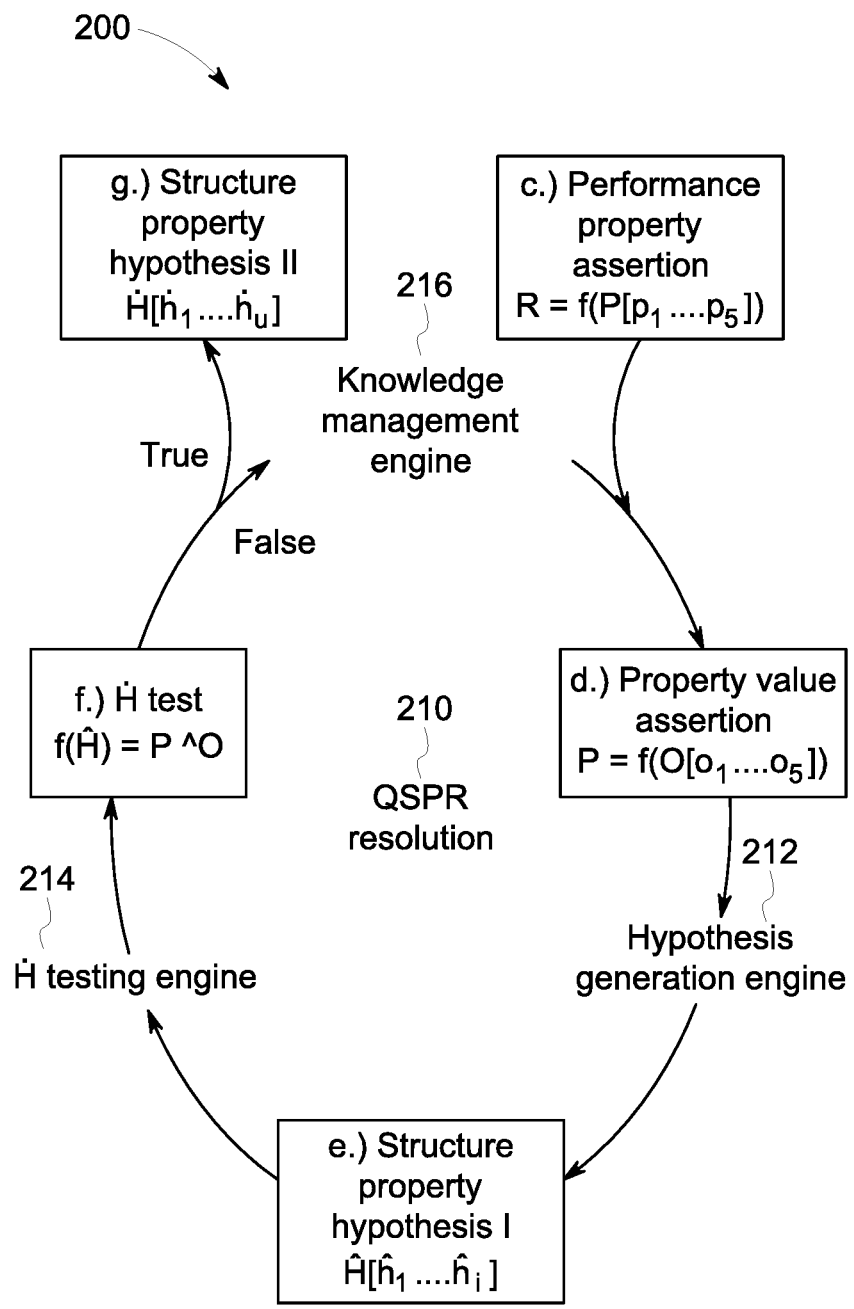
Figure 2C:
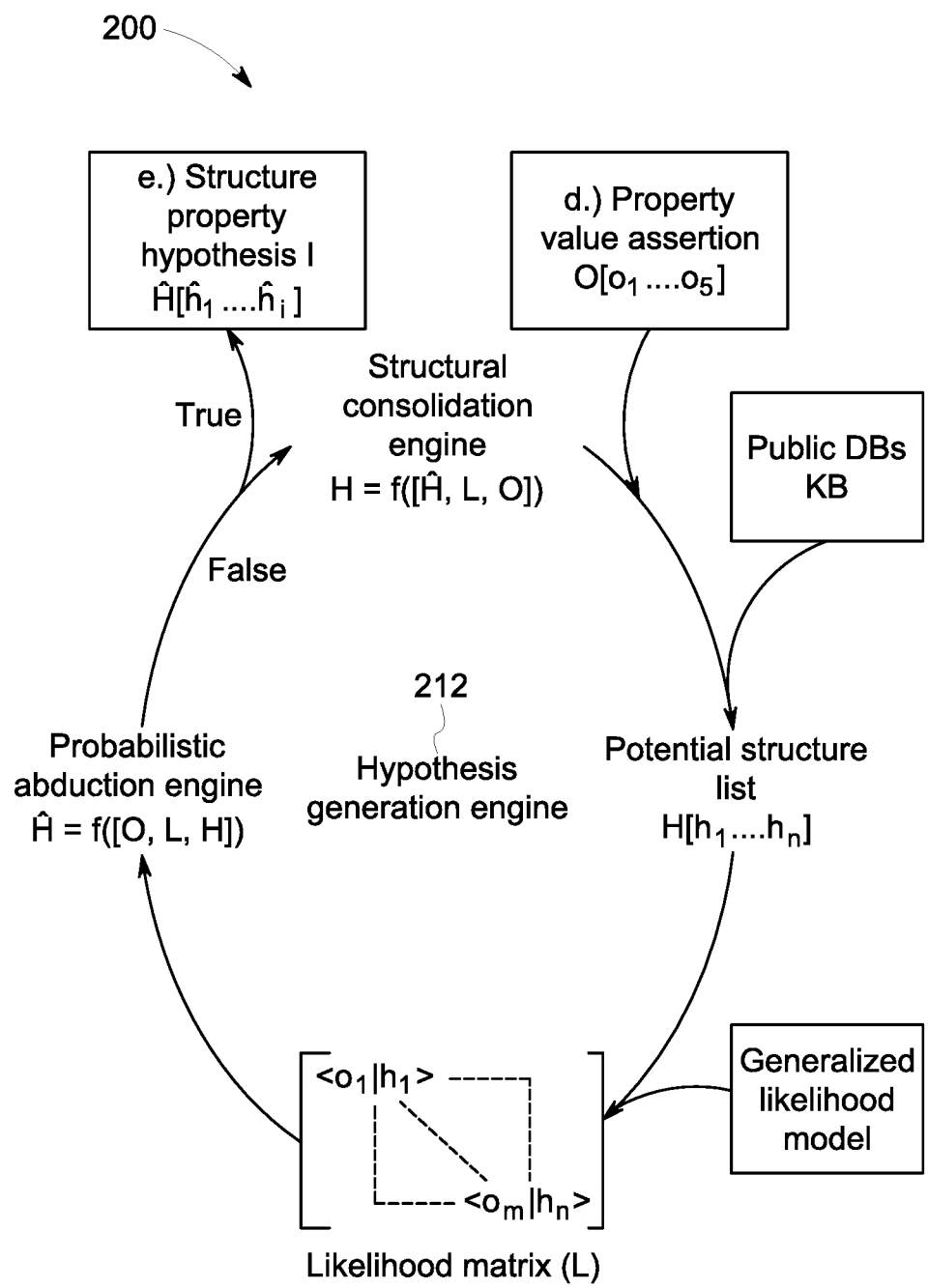
Figure 3:
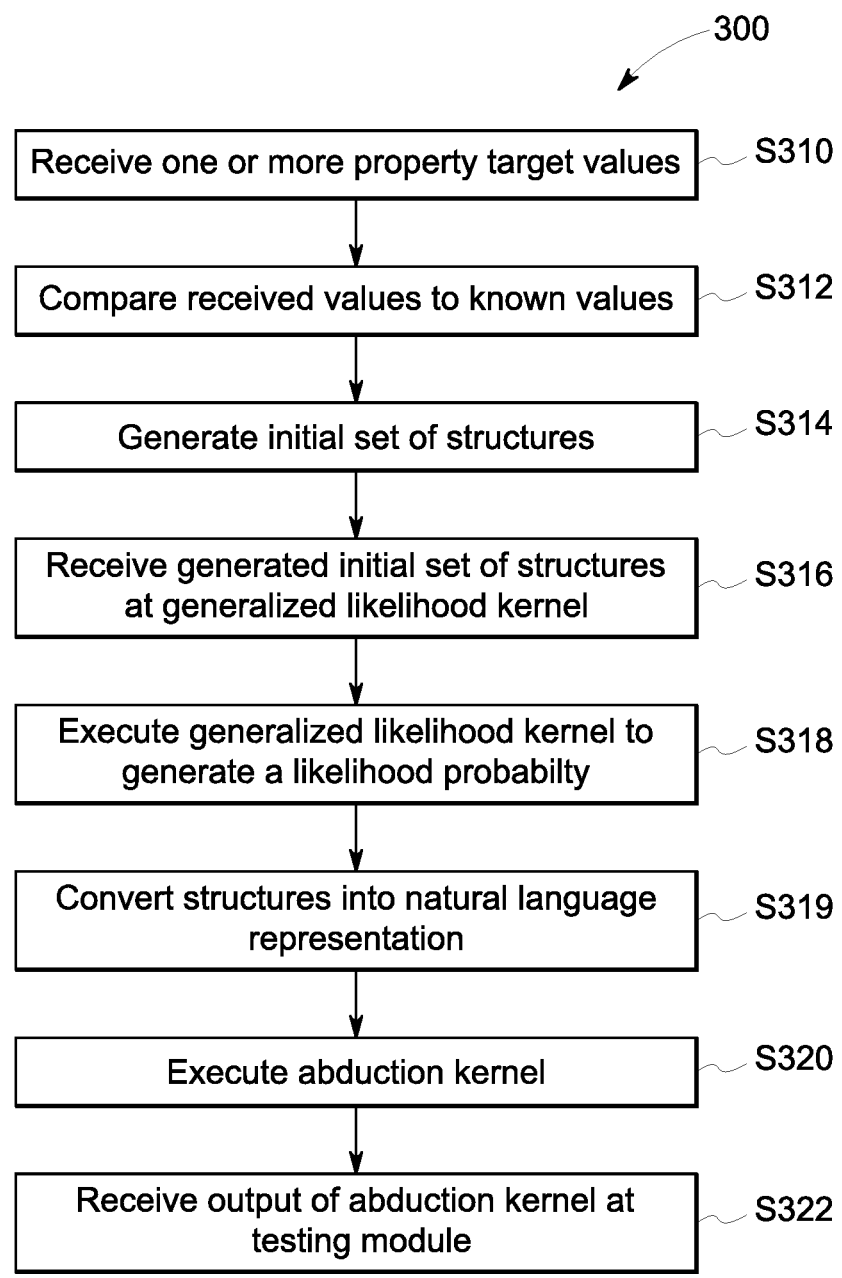
FIG. 3 is a method according to some embodiments.

Turning to FIGS. 1-9, a system 900 (FIG. 9) and diagrams of examples of operation according to some embodiments are provided. In particular, FIG. 3 provides a flow diagram of a process 300, according to some embodiments. Process 300, and any other process described herein, may be performed using any suitable combination of hardware (e.g., circuit(s)), software or manual means. For example, a computer-readable storage medium may store thereon instructions that when executed by a machine result in performance according to any of the embodiments described herein. In one or more embodiments, the system 900 is conditioned to perform the process 300 such that the system is a special-purpose element configured to perform operations not performable by a general-purpose computer or device. Software embodying these processes may be stored by any non-transitory tangible medium including a fixed disk, a floppy disk, a CD, a DVD, a Flash drive, or a magnetic tape. Examples of these processes will be described below with respect to embodiments of the system, but embodiments are not limited thereto. The flow charts described herein do not imply a fixed order to the steps, and embodiments of the present invention may be practiced in any order that is practicable.

A block diagram of an overview of a process 100 according to some embodiments is provided in FIG. 1. FIG. 1 shows how a user (not shown) (e.g., chemist) may use the HGE 212 to aid in discovering, as a non-exhaustive example, a new electrolyte for next generation lithium ion batteries. With the HGE 212 as an assistant, the user may focus on analyzing the lithium ion battery system and identifying the key areas where a chemical solution may have an impact, in this case the electrolyte. Once the user has reduced the problem to a set of target physical properties (observation set 106) for an application of the battery, the user may execute the HGE 212 to discover at least one molecule that meets the requirement. In one or more embodiments, the molecule may have an atomic mass in the range of 1 to 500 amu; in the range of 1 to 5000 amu; and in the range of 1 to 5000 amu. The HGE 212 may propose molecular structures as hypotheses (hypothesis set 108) that satisfy the properties asserted by the user (e.g., observation set 106). As described below, these proposed molecular structures may include known molecules with some of the asserted properties, such that each of the asserted properties is represented by at least one hypothesis. The hypothesis set 108 may be received by a structure generation model that may reduce the number of proposed molecules by at least one of: 1. determining whether any of the proposed molecular structures account for more than one of the asserted properties, and 2. generating new molecular structures. The output of the structure generation model may be a new molecular structure hypothesis set 112. Then, tests 114 (e.g., via chemist, literature, world models, robot chemists) may be executed with the new molecular structure hypothesis set 112, where the tests return actual observed properties. By iterating through a hypothesis/test loop (e.g., process 100), the HGE 212 scans chemical space and returns synthesized compounds and lists of potential target compounds that satisfy the asserted properties. As used herein, the terms "asserted property values" and "property target values" may be used interchangeably.

FIGS. 2A-2C provide an epistemology of the molecular discovery reasoning workflow 200 according to one or more embodiments. The workflow 200 maps from a given property value assertion 402 (FIG. 4) through a set of conditional hypotheses and hypothesis tests that lead to the conclusion: a performant ("target") molecule 201. In one or more embodiments, there are at least four conditional hypotheses that arise in the targeted molecular discovery process. The first is the general hypothesis that the performance of a given molecule ("system") is governed by the chemo-physical properties of a system element. This may be referred to as the molecular performance hypothesis 202. Note in FIG. 2A that the molecular performance hypothesis is not tested; rather it is the property value assertion 402 asserted by the user. The second conditional hypothesis is that a particular subset of properties out of all possible chemo-physical properties of the system element are the governing properties. This may be referred to as the performance property hypothesis 204. The third conditional hypothesis is that a set of target values, or value ranges, for the governing properties will yield desirable performance. This may be referred to as the property value hypothesis 206. The fourth conditional hypothesis is that a particular structure has the governing properties and the target property values. This may be referred to as the structure property hypothesis parts I and II 208. Each of these hypotheses are conditioned on the prior conditional hypothesis and ALL must hold true for a molecular discovery to have successfully hit the intended target of the performant molecule.

In one or more embodiments, the HGE 212 may be an autonomous agent that performs the actions from FIG. 2A items "d" to "f" in a continuous loop amounting to reasoning over a quantitative structure property relationship (QSPR). The HGE 212 may achieve an optimal resolution of the QSPR process given a user's property value assertion 402. In one or more embodiments, the HGE 212 may also perform the actions from "b" to "h" in a continuous loop via an artificial intelligence approach.

FIG. 2B shows a general process for the HGE 212 with reference to key system components. It is noted that, in one or more embodiments, the components may be extensible so that they may be reused. In one or more embodiments, the HGE 212 may include a QSPR resolution engine 210. The QSPR resolution engine 210 may receive from the user an assertion that a collection of properties P map to system performance R and that a collection of observable values O are the target values 402 for any given structure $\hat{h}_t$ in a set of proposed structures ($\hat{H}$). The system 100 may then make use of three system components to resolve the QSPR problem: (e.g., problem received by the QSPR resolution engine 210, and in particular, given a property, provide a structure) the Hypothesis Generation Engine 212, the Structure Testing Engine/Module 214, and the Knowledge Management Engine/Module 216. The HGE 212 may be tasked, in one or more embodiments, with learning the relationships of the observable property values to molecular structure as a continuous learning agent. The HGE output 902 (FIG. 9) may be a set of tested structures ($\hat{H}$) that includes both a set of molecular targets and a set of synthesized compounds, where the setoff tested structures all have the properties and property values asserted in O, an updated generalized likelihood model, and an updated knowledge base.

It is noted that the HGE 212 may iteratively explore a chemical space and find the most diverse set of structures that satisfy the asserted property values, and the HGE 212 will continuously learn.

Turning to FIG. 3, a process 300 for generating structural hypotheses for testing is provided. Initially, at 310, one or more property target values 402 (FIG. 4) for a material are received as input 902 at the HGE 404.

In one or more embodiments, the HGE 404 may include an abduction kernel 416. As described further below, the abduction kernel 416 may find structures that have the most coverage of the property set or may generate structures more likely to cover the full property set. In particular, the hypothesis generation engine ("HGE") 404 may generate a set of hypothetical structures (H) with the highest likelihood of having all of the properties in O.

Next, in S312, the HGE 404 executes an analysis by comparing the one or more received property target values to known values 908 in a knowledge base 906. A knowledge base engine 910 may search one or more publicly available databases and its internal knowledge base 906 for structural candidates that partially match the received property target values 902.

It is noted that knowledge extraction from jargon rich technical writings may require extracting information of similar accuracy across multiple, niche vocabularies. Different journals, corresponding to different chemical areas, may use their own domain-specific language, which may cause confusion in the generated output. Each extracted relationship may therefore be verified by linking it back to existing knowledge bases. One or more embodiments may apply semi-supervised methods for extracting information from social media sources combined with methods for claim verification that do not require human labeled data to make these links.

In one or more embodiments, the knowledge base engine 910 may execute a single value search in the knowledge base 906 based on all of the received property target value input 902. With the single value search, each structure identified by the knowledge base engine 910 matches one of the property target value input. Other suitable value searches may be executed. As in the non-exhaustive single value search example described above, the three received property target values are a boiling point of 110 degrees Celsius, a molar solubility greater than 10 mol/dm$^3$ and a UV absorbance 400 nanometers. The knowledge base engine 910 may retrieve from the knowledge base 906 (or other source): 1. all of the structures with a boiling point near 110 degrees Celsius; 2. all of the structures with a molar solubility near greater than 10 mol/dm$^3$; and 3. all of the structures with a UV absorbance near 400 nm. It is noted that, in one or more embodiments, the knowledge base engine 910 may pull exact matches in addition to non-exact matches. It is further noted that, in one or more embodiments, a threshold may be set to define which values constitute being "near" the property target value inputs.

Then, in S314, an initial set of hypothetical structures (H) 406 is generated by pooling together the structures retrieved by the knowledge base engine 910. The initial set of hypothetical structures (H) 406 may include, in one or more embodiments, one or more candidate structures/materials, where each candidate includes at least one property target value. It is noted that there may be a scenario where the knowledge base does not include any structures that match/substantially match one of the property target values. In these scenarios, the knowledge base engine 910 may return to the scientific literature to search, in an automated way, the limits of available knowledge. In one or more embodiments, the initial set of hypothetical structures (H) 406 may have a maximum likelihood of having only a subset of the property values in O, ($\mathcal{L}(o_j|h_j)$).

The initial set of hypothetical structures 406 is then received by a generalized likelihood kernel 408 in S316. The generalized likelihood kernel 408 may generate a probability each structure has of having a particular property. The generalized likelihood kernel 408 is then executed in S318 to generate a likelihood probability 410 for each candidate structure. In one or more embodiments, the likelihood probability may be stored in a likelihood matrix 412. The likelihood probability 410 is a measure of the likelihood that the candidate structure will have just one of the respective properties (e.g., the individual likelihood for each structure having a respective property. It is noted that the probability of each candidate structure having a second target property value may be a separate and independent property that may be calculated by the HGE 404 as a joint probability from each column of a probability matrix. The HGE 404 may use a generalized likelihood model (GLM) 414 to estimate the likelihood that a given structure has the asserted property. The GLM 414 may be trained to yield property likelihoods with any structure-property dataset. The GLM 414 may be a custom designed Deep Learning network using a Long Term-Short Term Memory (LSTM) model that converts SMILES strings to a common embedding of molecular features. The common embedding then provides input for neural network models that will predict the likelihood of a property given a structure and generate a property likelihood matrix (L) 412.

Figure 5:
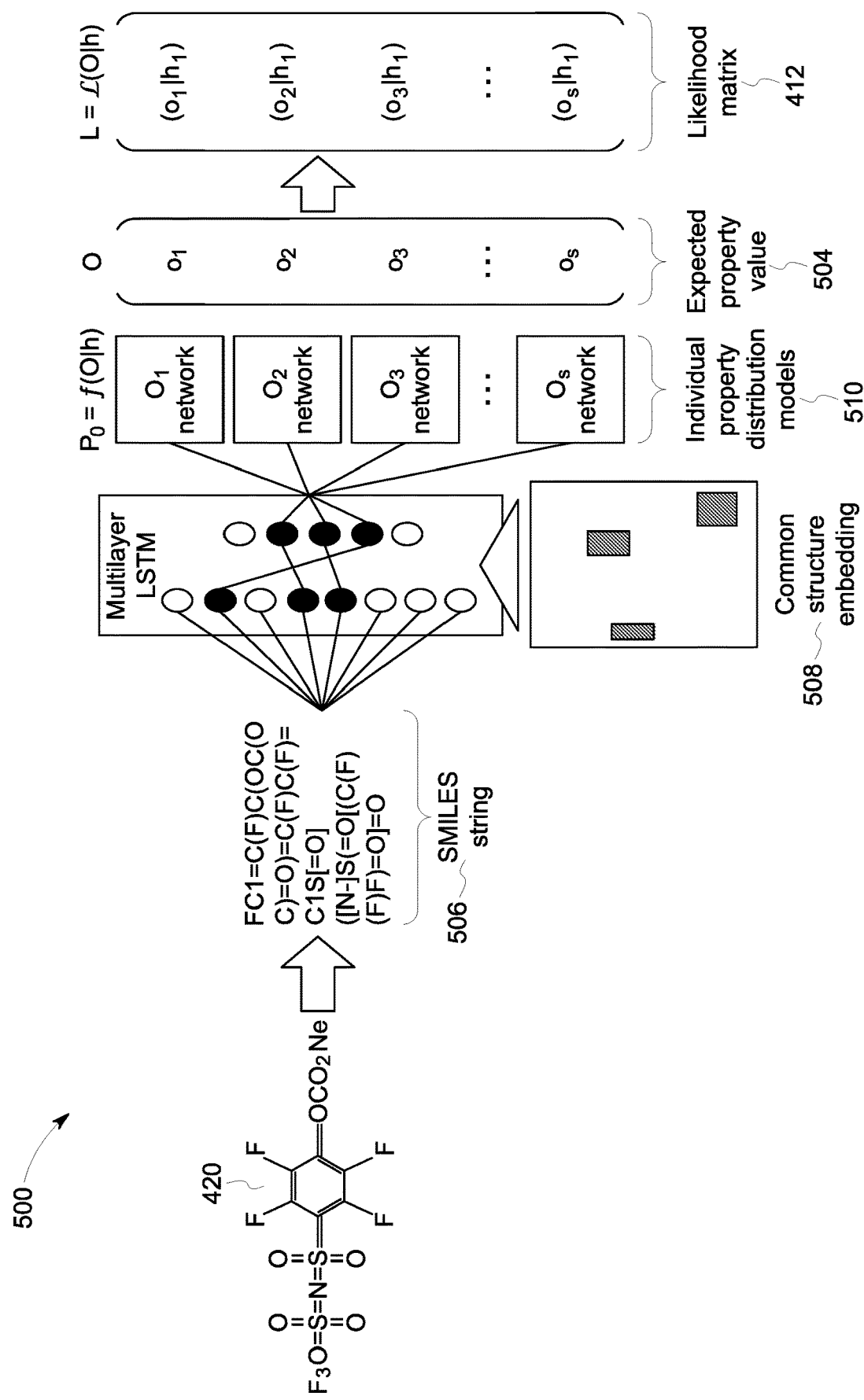
FIG. 5 is a block diagram of a process according to some embodiments.

In one or more embodiments, to effectively learn and execute the generalized likelihood probabilities at scale, a Deep Learning (DL) model 500, shown in FIG. 5 may be used to capture the conditional distributions from training data used to train the GLM 414. The DL model 500 in FIG. 5 may provide the architecture to predict property value likelihoods given a structure 502 and a property target values 504 ("expected property value"). The DL model 500 may ingest SMILES strings 506 and generate an intermediate embedding 508 and from that embedding 508 learns the parameters of a parameterized distribution layer 510. The DL model may then be evaluated to determine how likely a given compound is to satisfy each of the desired properties via the likelihood matrix 412.

Figure 6:
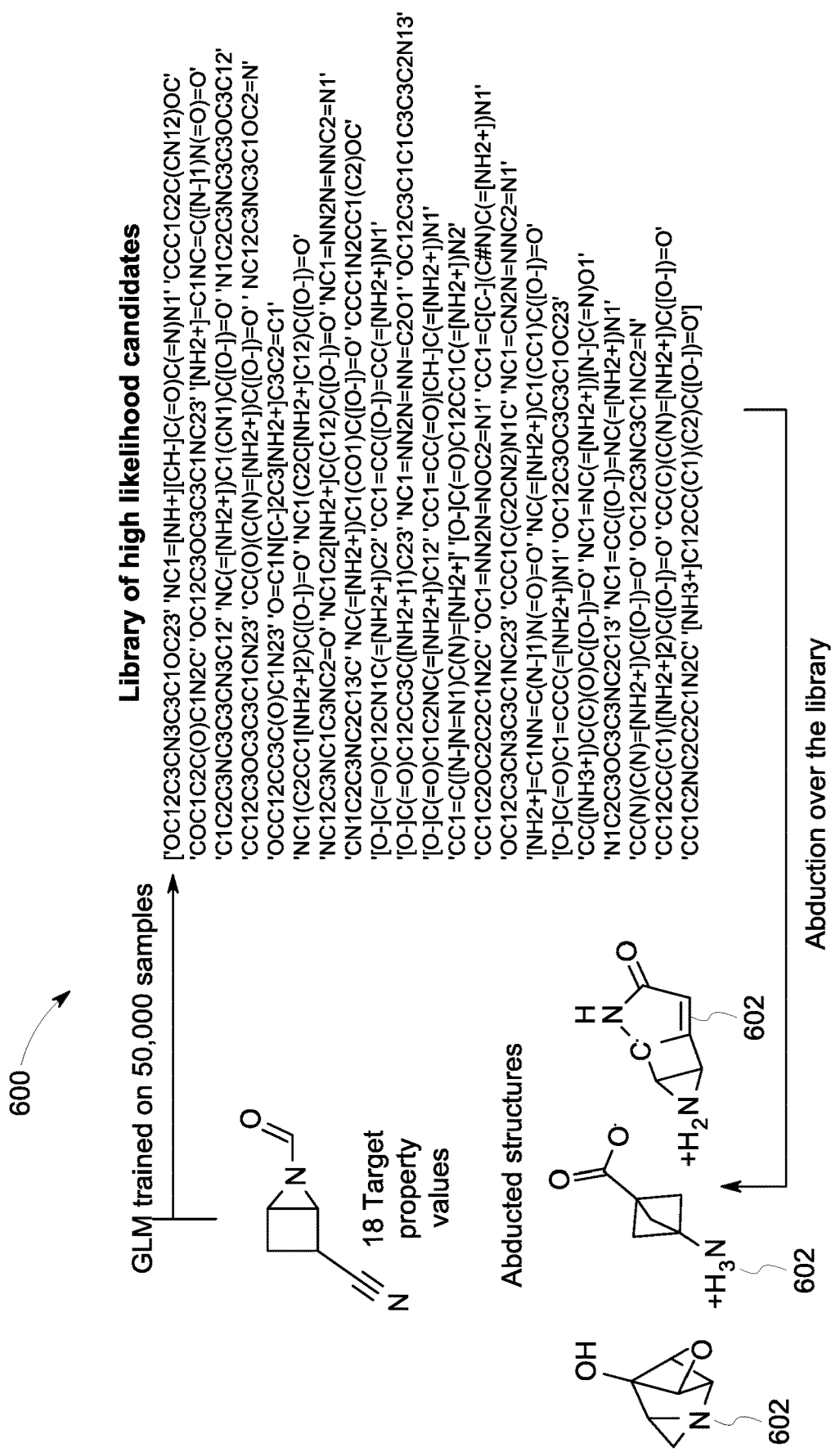
FIG. 6 is a non-exhaustive likelihood example according to some embodiments.
Figure 7:
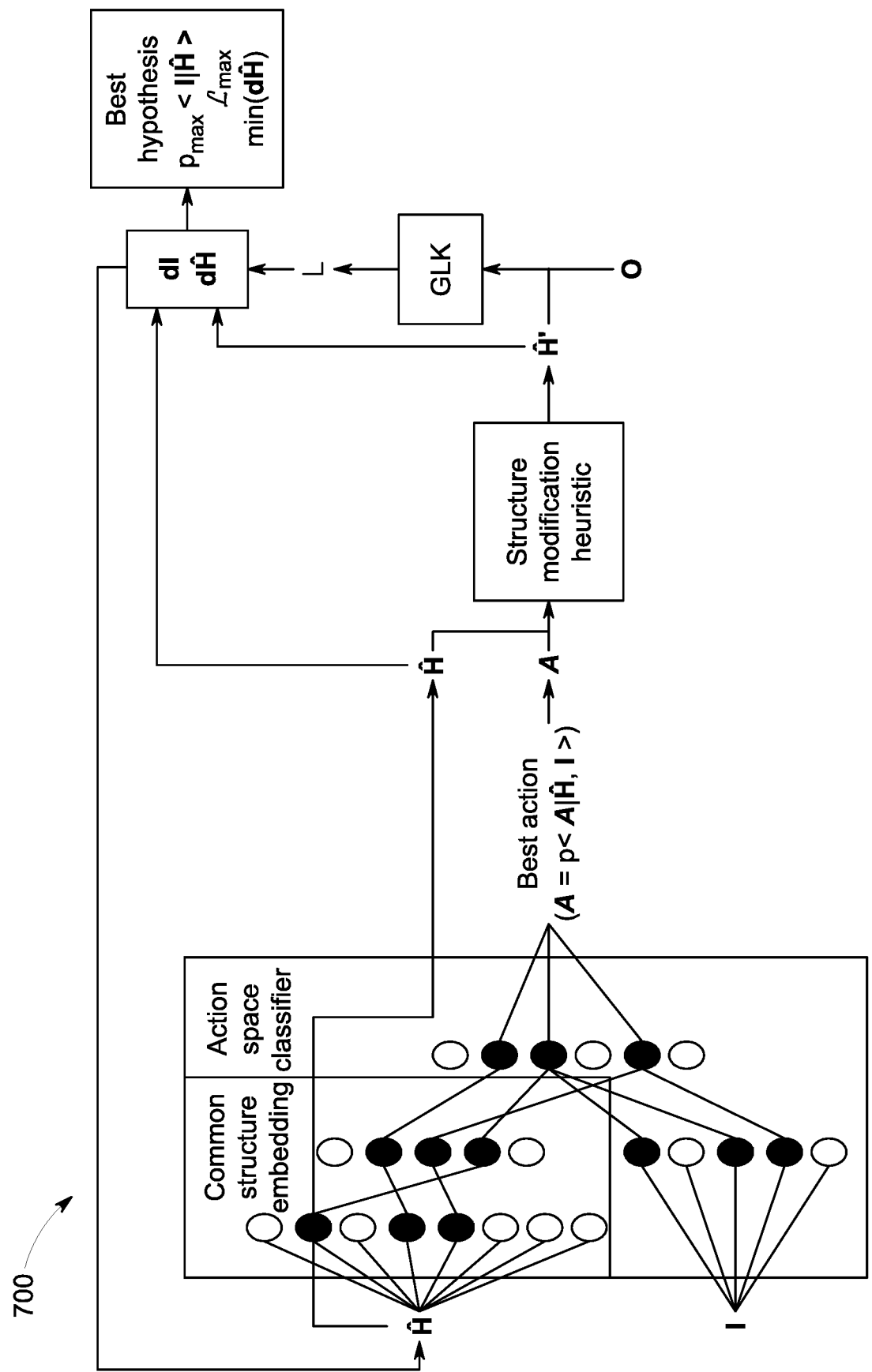
FIG. 7 is a non-exhaustive example including an action selection model according to some embodiments.

Turning to FIG. 6, initial results of generated property likelihoods is provided. Based on the property likelihoods it received from the GLM, the HGE 404 executes a natural language abduction process over the SMILES representation of high likelihood candidates in the abduction kernel 416. The abduction kernel 416 evaluates how well a structure or set of structures explains the target property set. Alternatively, the SMILES representation can be treated like a natural language and parsed allowing the abduction kernel to suggest molecular fragments that best explain the target property set. As shown herein, the abduction kernel 416 has output 904 three structures 602 that meet all eighteen property target values. In this non-exhaustive example, the GLM has been trained on 50,000 samples. These three structures may be taken as is, or further modified towards the target properties in the HGE.

The SMILES representation may be helpful to the abduction kernel as it is a Turing complete natural language representation of molecular structure. It is noted that other natural language representations of molecular structure may also be valid inputs for the abduction kernel 416. It is also noted that if more information is needed to create an adequate generalized structure-property embedding then that provided by the SMILES representation 506, network architectures that may accommodate three-dimensional (3D) molecular representations in the form of computationally derived point clouds for electron density, charge density, HOMO/LUMO densities, etc. may be used. It is further noted that the embedding space may exaggerate important differences in the structural input space, particularly when the 3D information is included.

Turning back to the process 300, in S319 each hypothetical structure is converted by the HGE 404 into a natural language representation. Then in S320 an abduction kernel 416 of the HGE 404 is executed on the natural language representation using the at least one generated probability to output at least one proposed structure that satisfies a likelihood threshold for having the property target value. The abduction kernel 416 may consolidate structural similarities and elaborate structural cores along physical property vectors. The abduction kernel 416 may generate a set of proposed structures ($\hat{H}$) with the maximum likelihood of having all of the desired property values given the structures in the initial set ($\mathcal{L}(O|\hat{H})$). In one or more embodiments, an output 418 of the abduction kernel 416 an abduced hypothesis. The abduced hypothesis may be at least one of: at least one proposed molecular structure that satisfies all of the asserted property values 402; and a minimal set of two or more proposed molecular structures that satisfies all of the asserted values 402. The abduction kernel 416 may allow the system 900 to reach likely target structures more quickly than conventional methods without requiring an exhaustive search of chemical space.

In one or more embodiments, the abduction kernel 416 may use an Etcetera abduction formalism and LISP to solve the abduction problem of what structure is causing the desired properties (e.g., $\hat{H}$ has desired properties, but don't know why it has these properties and don't know what structure (x) is causing these properties). It is noted that abduction is an open-ended (not closed) logical formalism that relies on an assertion. As the abduction is open ended, the system may extrapolate structures, leading to novel solutions. Transforming chemical structures into a natural language then provides for the use of abductive logic formalisms (e.g., Etcetera) and a solver (e.g., LISP) to solve the abduction problem. The abduction kernel 416 may use the output of the generalized likelihood kernel 408 described above, and an output of a structure generation kernel 420 (e.g., a molecular structure modification model), described below, in order to yield, using the knowledge base 906, novel structures for testing.

Figure 4:
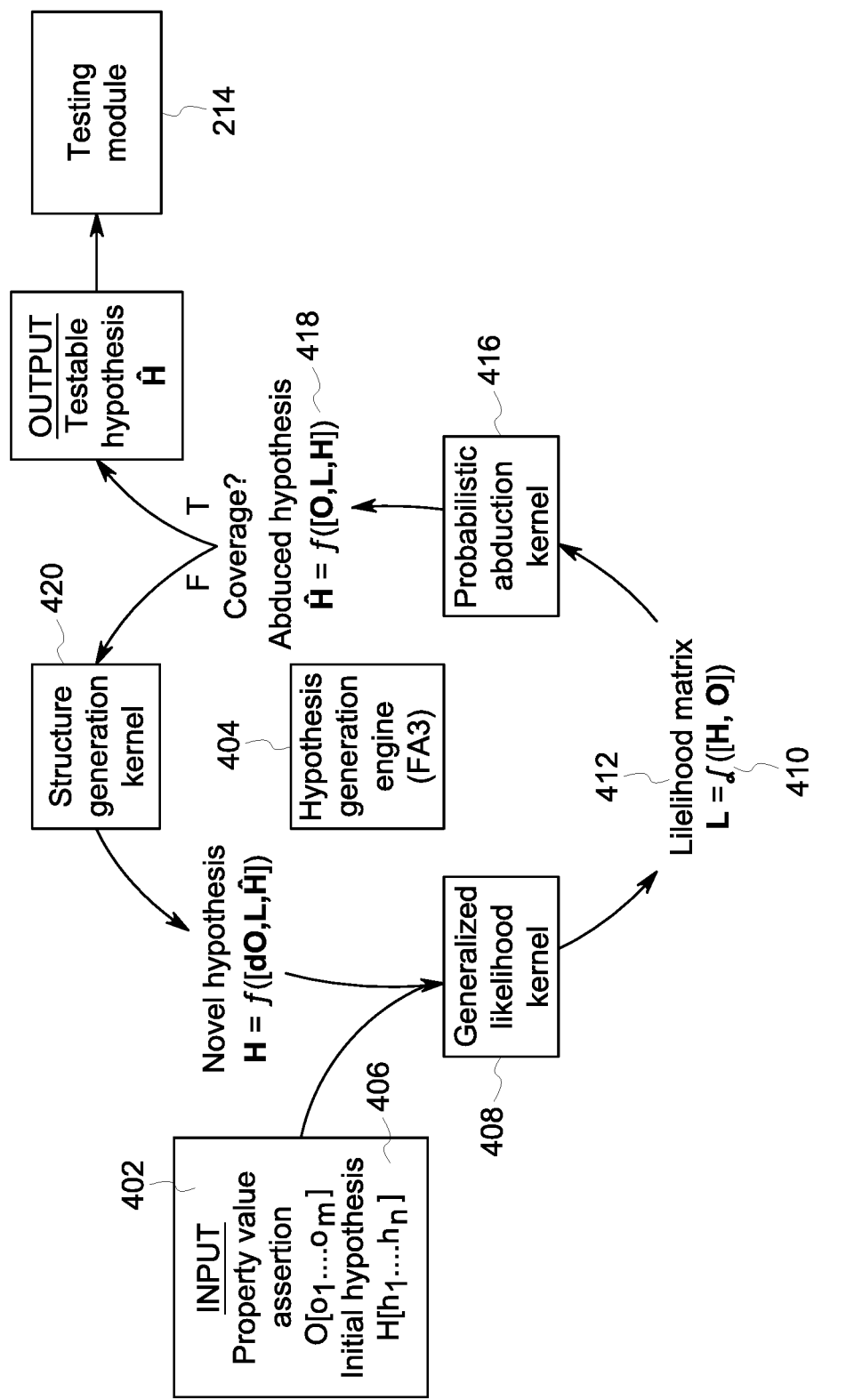
FIG. 4 is a block diagram of a process according to some embodiments

With respect to structure generation kernel 420, in one or more embodiments, the structure generation kernel 420 may predict structural modifications that are most likely to perturb the properties in the direction of the structure having the asserted property values ("target"). In one or more embodiments, the structure generation kernel 420 may accept the common embedding from the GLM. The structure generation kernel 420 may be trained to generate structural modifications expected to modify the observed properties towards the target. In one or more embodiments, the generated one or more structural modifications may be analyzed as compared to the knowledge base. The components of the HGE 404 may continue to cycle until a set of structures are found that have a sufficient likelihood of covering the property set. For example, as shown in FIG. 4, after the structure generation kernel 420 generates one or more novel structures 422, these novel structures 422 may be received by the generalized likelihood kernel 408, and the process 300 may be repeated as from S316.

The generation of novel structures is optimally done along a physical property trajectory, rather than a massive grid of all possible structures. In one or more embodiments, this problem is formulated as a Markov-Decision Process where structural modification actions (A) are taken to create new structures (Ĥ) in order to maximize a reward ($\mathcal{L}_{max}, d\hat{H}_{min}$). Examples of structural modification actions include adding or removing pendant functional groups, carbocyclic ring expansion or contraction, heterocyclic ring expansion or contraction, ring opening or closing, or single atom substitutions. The reward in this embodiment is the joint property likelihood calculated from the output provided by the GLM. Given this formulation, a policy 700, or action-space classification model 912, is learned for taking actions that maximize the joint probability of having all target values for a structural class given by the abduction kernel.

One or more embodiments provide for the structure generation kernel 420 to include an action space classification model 912 that uses the common structure-property embedding from the generalized likelihood model (GLM) 414 to select appropriate structure modifications given directional change in properties. The common embedding from the GLM 414 may provide the molecular representation and a unit vector (I) will set the direction in property space. The action space classification model 912 may use a heuristic kernel to adhere to constraints for a given structure such as synthetically plausible locations for structural modification, constraints for synthetic accessibility on an autonomous testing platform, or constraints provided by the abduction kernel for structural motifs that must be conserved. Ultimately, the action space classifier model 912 may output the probability that a modification to the structure will move the chemical property in the desired unit direction (I), which may be akin to a chemist/user reasoning through structure modifications using basic linear free energy relationships. The top structural modifications above a threshold likelihood of having the asserted properties are then selected to output a set of testable molecular structures. It is noted that the goal of the HGE is to select a testable molecular hypothesis, and not a validated molecular solution.

Figure 8:
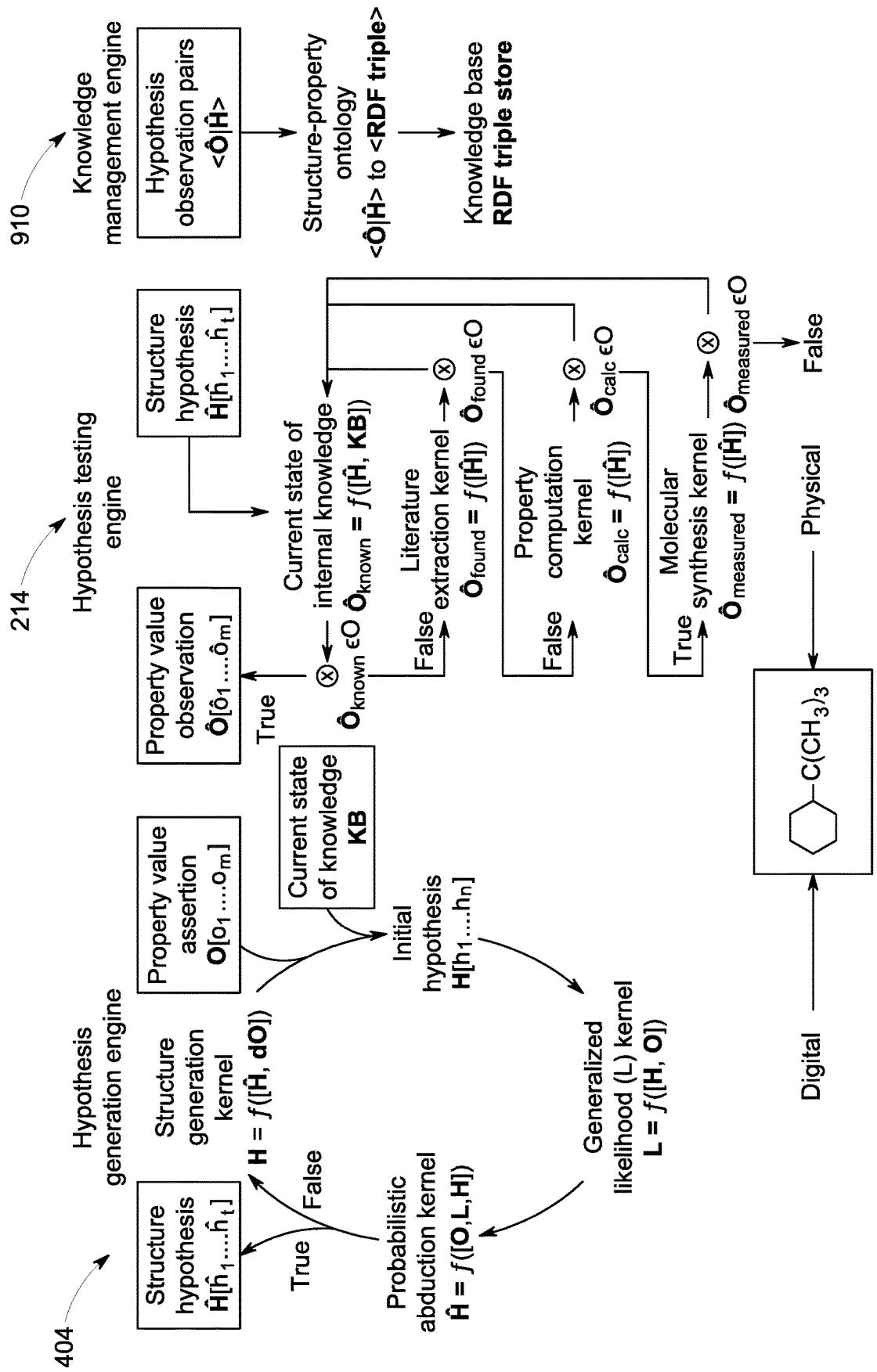
FIG. 8 is block diagram of several processes according to some embodiments.

Turning back to the process 300, in S322, the output of the executed abduction kernel 416 is received at a testing module 214. In one or more embodiments, when a probability that the abduced hypothesis 418 satisfies a pre-determined amount of the target property values is above a threshold value, the output may be tested at the testing module 214. Otherwise, when the probability that the abduced hypothesis 418 satisfies the pre-determined amount of target property values is below the threshold value, the output may be received at the structure generation kernel 420, as described above. The testing module 214 may accept the set of structural hypotheses from the HGE 404 and generate a subset of structures (Ĥ) that pass a simple T-test for having the target property values in O. As shown in FIG. 8, the testing module 214 may synthesize a physical molecular structure based on the output of the HGE. This synthesized structure may then be analyzed to determine whether the physical structure meets the digital property assertions. The testing module 214 may make use of at least one of the following testing processes: automated literature searching methods, automated computational methods for property estimation, and automated synthetic and characterization methods to provide the ground-truth properties and their distributions for evaluation against target. Other suitable testing processes may be used by the testing module 214.

Figure 9:
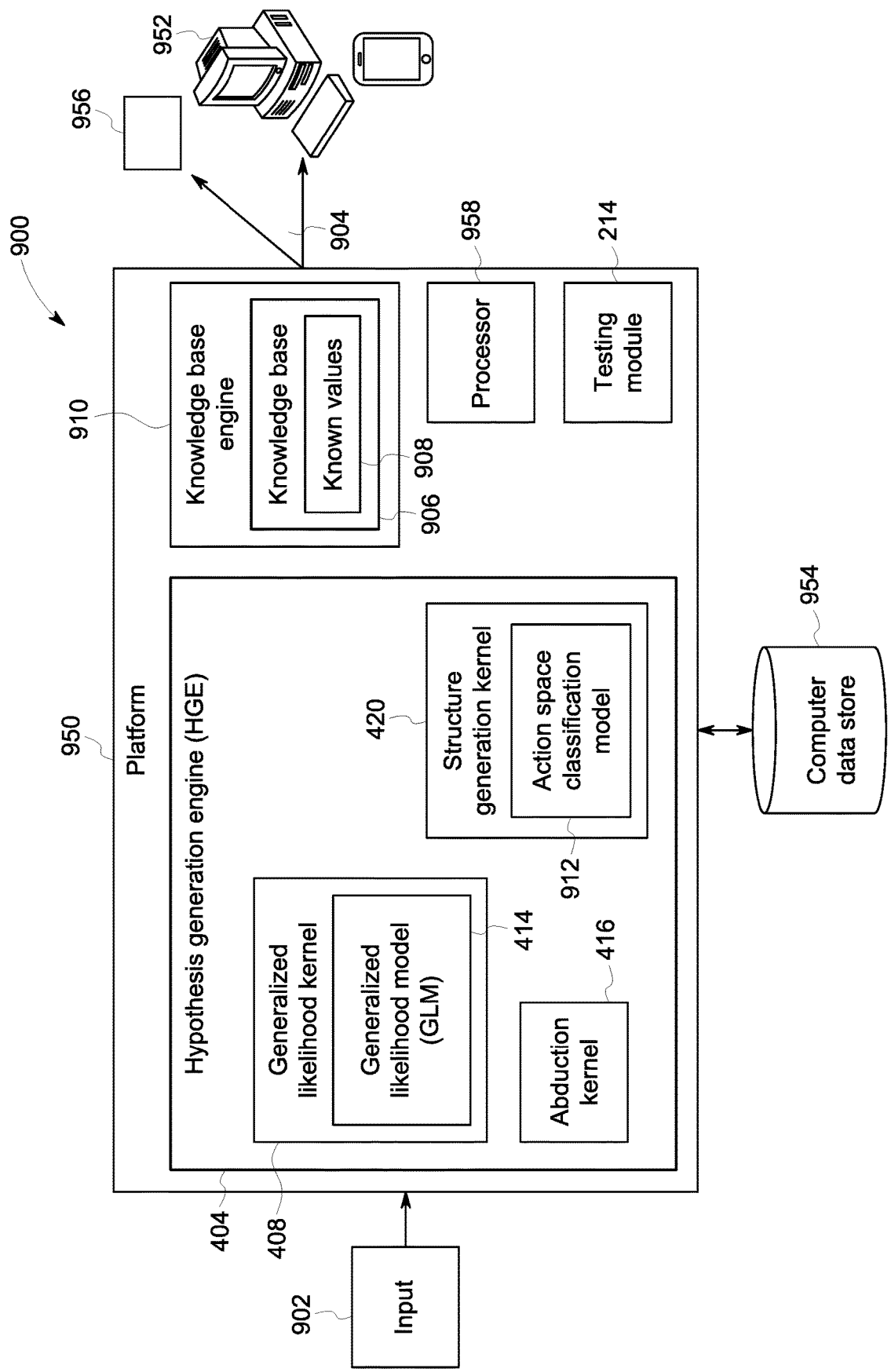
FIG. 9 is a block diagram of a system according to some embodiments

FIG. 9 is a block diagram of system architecture 900 according to some embodiments. Embodiments are not limited to architecture 900.

Architecture 900 includes a platform 950, a HGE 404, a user platform 952, a data store 954 (e.g., database). In one or more embodiments, the HGE 404 may reside on the platform 950. Platform 950 provides any suitable interfaces through which users/other systems 956 may communicate with the HGE 404.

In one or more embodiments, the output of the HGE 404 may be output to a user platform 952 (a control system, a desktop computer, a laptop computer, a personal digital assistant, a tablet, a smartphone, etc.) to view information about the proposed structures. In one or more embodiments, the output from the HGE 404 may be transmitted to various user platforms or to other system (956), as appropriate (e.g., for display to, and manipulation by, a user, further analysis and manipulation).

In one or more embodiments, the system 900 may include one or more processing elements 958 and a memory/computer data store 954. The processor 958 may, for example, be a microprocessor, and may operate to control the overall functioning of the HGE 404. In one or more embodiments, the HGE 404 may include a communication controller for allowing the processor 958 and hence the HGE 404, to engage in communication over data networks with other devices (e.g., user interface 952 and other system 956).

In one or more embodiments, the system 900 may include one or more memory and/or data storage devices 954 that store data that may be used by the module. The data stored in the data store 954 may be received from disparate hardware and software systems, some of which are not inter-operational with one another. The systems may comprise a back-end data environment employed by a business, industrial or personal context.

In one or more embodiments, the data store 954 may comprise any combination of one or more of a hard disk drive, RAM (random access memory), ROM (read only memory), flash memory, etc. The memory/data storage devices 954 may store software that programs the processor 958 and the HGE 404 to perform functionality as described herein.

As used herein, devices, including those associated with the system 900 and any other devices described herein, may exchange information and transfer input and output ("communication") via any number of different systems. For example, wide area networks (WANs) and/or local area networks (LANs) may enable devices in the system to communicate with each other. In some embodiments, communication may be via the Internet, including a global internetwork formed by logical and physical connections between multiple WANs and/or LANs. Alternately, or additionally, communication may be via one or more telephone networks, cellular networks, a fiber-optic network, a satellite network, an infrared network, a radio frequency network, any other type of network that may be used to transmit information between devices, and/or one or more wired and/or wireless networks such as, but not limited to Bluetooth access points, wireless access points, IP-based networks, or the like. Communication may also be via servers that enable one type of network to interface with another type of network. Moreover, communication between any of the depicted devices may proceed over any one or more currently or hereafter-known transmission protocols, such as Asynchronous Transfer Mode (ATM), Internet Protocol (IP), Hypertext Transfer Protocol (HTTP) and Wireless Application Protocol (WAP).

The embodiments described herein may be implemented using any number of different hardware configurations.

Figure 10:
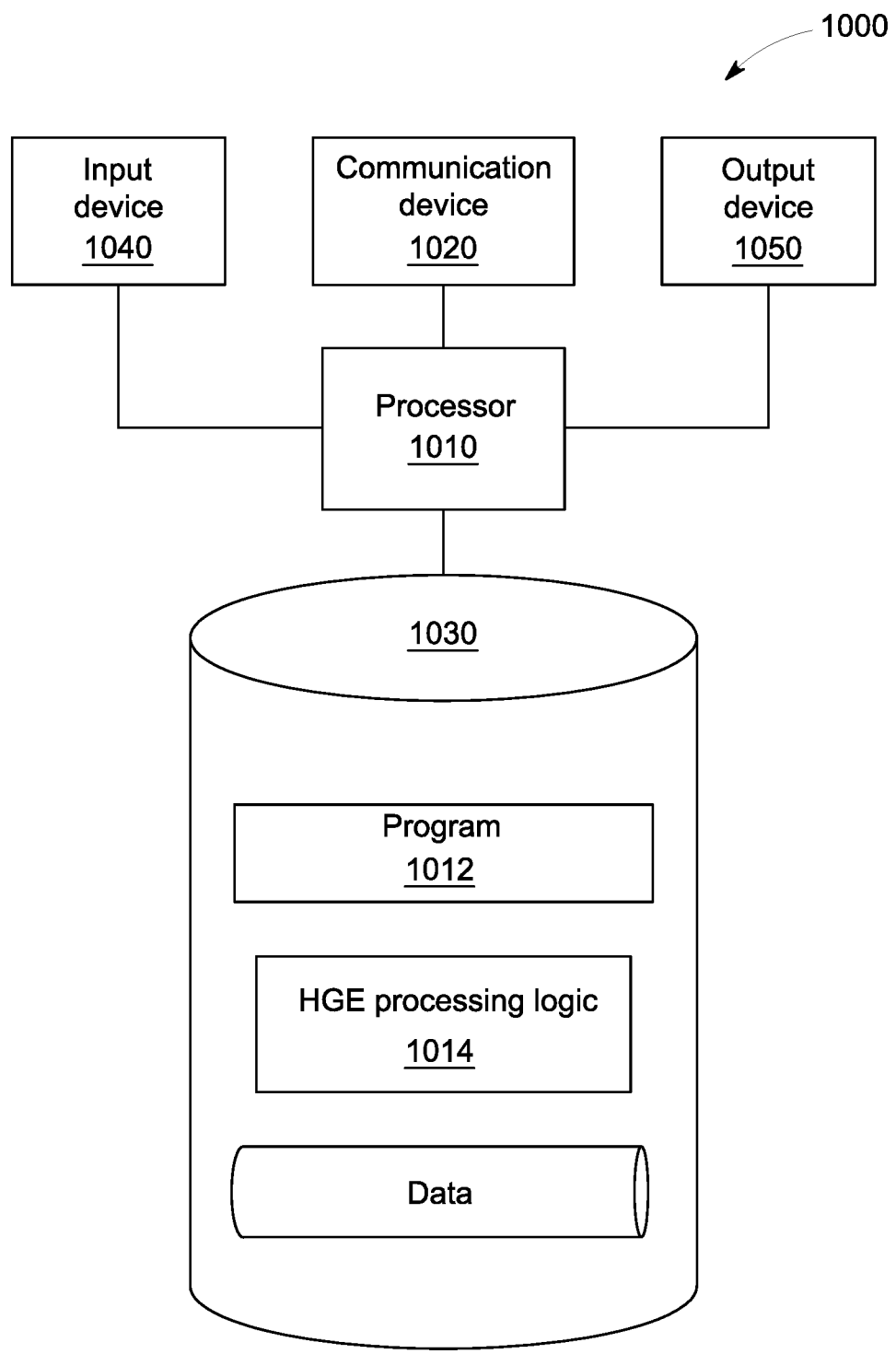
FIG. 10 is a block diagram of a development platform according to some embodiments.

Note the embodiments described herein may be implemented using any number of different hardware configurations. For example, FIG. 10 illustrates an HGE platform 1000 that may be, for example, associated with the system 900 of FIG. 9. The HGE platform 1000 may be implemented using any architecture that is or becomes known, including but limited to distributed, on-premise, cloud-based and hybrid architectures, as well as embedded in another system. Embodiments are not limited to HGE platform 1000.

The HGE platform 1000 comprises an HGE processor 1010 ("processor"), such as one or more commercially available Central Processing Units (CPUs) in the form of one-chip microprocessors, coupled to a communication device 1020 configured to communicate via a communication network (not shown in FIG. 10). The communication device 1020 may be used to communicate, for example, with one or more users. The HGE platform 1000 further includes an input device 1040 (e.g., a mouse and/or keyboard to enter information) and an output device 1050 (e.g., to output the outcome of module execution).

The processor 1010 also communicates with a memory/storage device 1030. The storage device 1030 may comprise any appropriate information storage device, including combinations of magnetic storage devices (e.g., a hard disk drive), optical storage devices, mobile telephones, and/or semiconductor memory devices. The storage device 1030 may store a program 1012 and/or HGE processing logic 1014 for controlling the processor 1010. The processor 1010 performs instructions of the programs 1012, 1014, and thereby operates in accordance with any of the embodiments described herein. For example, the processor 1010 may receive data and then may apply the instructions of the programs 1012, 1014 to determine molecules with desired physical properties.

The programs 1012, 1014 may be stored in a compressed, uncompiled and/or encrypted format. The programs 1012, 1014 may furthermore include other program elements, such as an operating system, a database management system, and/or device drivers used by the processor 1010 to interface with peripheral devices.

As used herein, information may be "received" by or "transmitted" to, for example: (i) the platform 1000 from another device; or (ii) a software application or module within the platform 1000 from another software application, module, or any other source.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It should be noted that any of the methods described herein can include an additional step of providing a system comprising distinct software modules embodied on a computer readable storage medium; the modules can include, for example, any or all of the elements depicted in the block diagrams and/or described herein. The method steps can then be carried out using the distinct software modules and/or sub-modules of the system, as described above, executing on one or more hardware processors 1010 (FIG. 10). Further, a computer program product can include a computer-readable storage medium with code adapted to be implemented to carry out one or more method steps described herein, including the provision of the system with the distinct software modules.

This written description uses examples to disclose the invention, including the preferred embodiments, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. Aspects from the various embodiments described, as well as other known equivalents for each such aspects, can be mixed and matched by one of ordinary skill in the art to construct additional embodiments and techniques in accordance with principles of this application.

Those in the art will appreciate that various adaptations and modifications of the above-described embodiments can be configured without departing from the scope and spirit of the claims. Therefore, it is to be understood that the claims may be practiced other than as specifically described herein.

The invention claimed is:

1. A system comprising:
a Hypothesis Generation Engine (HGE) to receive one or more property target values for a material;
a memory for storing program instructions;
an HGE processor, coupled to the memory, and in communication with the HGE, and operative to execute program instructions to:
receive the one or more property target values for the material;
analyze the one or more property target values as compared to one or more known values in a knowledge base;
generate, based on the analysis, an initial set of hypothetical structures, wherein each hypothetical structure includes at least one property target value;
execute a likelihood model for each candidate material to generate a likelihood probability for each hypothetical structure, wherein the likelihood probability is a measure of the likelihood that the hypothetical structure will have the target property value;
convert each hypothetical structure into a natural language representation;
execute an abduction kernel on the natural language representation with the at least one likelihood probability, to output at least one proposed structure that satisfies a likelihood threshold for having the property target value; and
receive the output of the executed abduction kernel at a testing module to determine whether the output satisfies the property target values.

2. The system of claim 1, further comprising program instructions to:
receive the output of the executed abduction kernel at a structure generation kernel prior to receiving the output at the testing module; and
generate one or more structural modifications of the output to maximize a property target value likelihood.

3. The system of claim 2, wherein the structure generation kernel generates the one or more structural modifications via a reinforcement learning process.

4. The system of claim 1, wherein the material is a molecule.

5. The system of claim 4, wherein the molecule has an atomic mass in the range 1 to 500 amu.

6. The system of claim 4, wherein the molecule has an atomic mass in the range 1 to 5000 amu.

7. The system of claim 4, wherein the molecule has an atomic mass in the range 1 to 50000 amu.

8. The system of claim 1, wherein when the likelihood probability is above the likelihood threshold, the proposed material associated with the output is tested at the testing module.

9. The system of claim 2, wherein when the likelihood probability is below the likelihood threshold, the output is received at the structure generation kernel.

10. The system of claim 9, wherein the generated one or more structural modifications of the proposed material are analyzed as compared to the knowledge base.

11. The system of claim 10, wherein the generation of one or more structural modifications is iterative until an endpoint is reached.

12. A computer-implemented method comprising:
receiving one or more property target values for a material;
analyzing the one or more property target values as compared to one or more known values in a knowledge base;
generating, based on the analysis, an initial set of hypothetical structures, wherein each hypothetical structure includes at least one property target value;
executing a likelihood model for each candidate material to generate a likelihood probability for each hypothetical structure, wherein the likelihood probability is a measure of the likelihood that the hypothetical structure will have the target property value;
convert each hypothetical structure into a natural language representation;
executing an abduction kernel on the natural language representation with the at least one likelihood probability, to output at least proposed structure that satisfies a likelihood threshold for having the property target value; and
receiving the output of the executed abduction kernel at a testing module to determine whether the output satisfies the property target values.

13. The method of claim 12 further comprising:
receiving the output of the executed abduction kernel at a structure generation kernel prior to receiving the output at the testing module; and
generating one or more structural modifications of the output to maximize a property target value likelihood.

14. The method of claim 13, wherein the structure generation kernel generates the one or more structural modifications via a reinforcement learning process.

15. The method of claim 12, wherein the material is a molecule.

16. The method of claim 13, wherein when the likelihood probability is below the likelihood threshold, the output is received at the structure generation kernel.

17. The method of claim 16, wherein the generation of one or more structural modifications is iterative until an endpoint is reached.

18. A non-transient, computer-readable medium storing instructions to be executed by a processor to perform a method comprising:
receiving one or more property target values for a material;
analyzing the one or more property target values as compared to one or more known values in a knowledge base;
generating, based on the analysis, an initial set of hypothetical structures, wherein each hypothetical structure includes at least one property target value;
executing a likelihood model for each candidate material to generate a likelihood probability for each hypothetical structure, wherein the likelihood probability is a measure of the likelihood that the hypothetical structure will have the target property value;
convert each hypothetical structure into a natural language representation;
executing an abduction kernel on the natural language representation with the at least one likelihood probability, to output at least proposed structure that satisfies a likelihood threshold for having the property target value; and receiving the output of the executed abduction kernel at a testing module to determine whether the output satisfies the property target values.

19. The medium of claim 18 further comprising:

receiving the output of the executed abduction kernel at a structure generation kernel prior to receiving the output at the testing module; and generating one or more structural modifications of the output to maximize a property target value likelihood.

20. The medium of claim 19, wherein the structure generation kernel generates the one or more structural modifications via a reinforcement learning process.

* * * * *